United States Patent [19]
Petrus

[11] Patent Number: 5,875,799
[45] Date of Patent: Mar. 2, 1999

[54] THERAPEUTIC DENTAL FLOSS FOR TREATING SYSTEMIC DISEASES

[75] Inventor: Edward J. Petrus, Austin, Tex.

[73] Assignee: Advanced Medical Instruments, Inc., Austin, Tex.

[21] Appl. No.: 935,841

[22] Filed: Sep. 23, 1997

[51] Int. Cl.$^6$ .................................................. A61C 15/00
[52] U.S. Cl. ............................ 132/323; 132/325; 424/49
[58] Field of Search ..................................... 132/321, 323, 132/324, 325, 326, 327, 328, 329; 424/49, 52, 54, 401; 433/215, 217.1

[56] References Cited

U.S. PATENT DOCUMENTS

| | | |
|---|---|---|
| Re. 33,465 | 11/1990 | Eby, III . |
| Re. 35,439 | 2/1997 | Rosenberger . |
| 3,771,536 | 11/1973 | Dragan ..................................... 132/321 |
| 3,897,795 | 8/1975 | Engel ....................................... 132/323 |
| 3,942,539 | 3/1976 | Corliss et al. . |
| 4,160,821 | 7/1979 | Sipos . |
| 4,229,430 | 10/1980 | Fahim et al. . |
| 4,325,939 | 4/1982 | Shah . |
| 4,414,990 | 11/1983 | Yost . |
| 4,503,070 | 3/1985 | Eby, III . |
| 4,548,219 | 10/1985 | Newman et al. . |
| 4,627,975 | 12/1986 | Lynch et al. . |
| 4,632,937 | 12/1986 | Lynch . |
| 4,638,823 | 1/1987 | Newman et al. . |
| 4,819,675 | 4/1989 | Wilkinson et al. . |
| 4,937,066 | 6/1990 | Vlock . |
| 4,941,487 | 7/1990 | VanBeneden . |
| 4,956,385 | 9/1990 | Eby, III . |
| 5,033,488 | 7/1991 | Curtis et al. ............................. 132/321 |
| 5,040,554 | 8/1991 | Rosenberger ........................... 132/321 |
| 5,065,861 | 11/1991 | Greene et al. ........................... 132/325 |
| 5,095,035 | 3/1992 | Eby, III . |
| 5,104,644 | 4/1992 | Douglas . |
| 5,129,824 | 7/1992 | Keller ..................................... 132/321 |
| 5,209,251 | 5/1993 | Curtis et al. . |
| 5,226,434 | 7/1993 | Britton et al. .......................... 132/321 |
| 5,280,796 | 1/1994 | Rosenberger . |
| 5,330,357 | 7/1994 | Keller . |
| 5,409,905 | 4/1995 | Eby, III . |
| 5,423,337 | 6/1995 | Ahlert et al. . |
| 5,456,902 | 10/1995 | Williams et al. ........................ 424/49 |
| 5,603,921 | 2/1997 | Bowen . |
| 5,616,313 | 4/1997 | Williams et al. ........................ 424/49 |
| 5,624,675 | 4/1997 | Kelly . |
| 5,632,972 | 5/1997 | Williams et al. . |
| 5,635,162 | 6/1997 | Fischer . |
| 5,665,333 | 9/1997 | Homola et al. ......................... 424/54 |

OTHER PUBLICATIONS

Beck, et al., "Periodontal Disease and Cardiovascular Disease," *J. Periodontol*, 67:1123–1137, 1996 (abstract only).

Charnow, "Probe implicates deep kissing in HIV case," *Medical Tribune*, Aug. 14, 1997 (abstract only).

Christensen, "Dental Infections May Increase Risk of Stroke," *Medical Tribune News Service,* Sep. 8, 1997 (abstract only).

Flemmig, et al., "Efficacy of systemically administered acetylsalicylic acid plus scaling on periodontal health and elastase–aplha 1–proteinase inhibitor in gingival crevicular fluid," *J. Clin. Periodoontol,* pp. 153–159, Mar. 23, 1996 (abstract only).

Joshipura, et al., "Poor oral health and coronary heart disease," *J. Dent. Res.,* 75(9):1631–6, Sep. 1996 (abstract only).

La Voie, A., "Material infection may be linked to cerebral palsy in newborns," *Medical Tribune,* Aug. 14, 1997 (abstract only).

Modica, P., "Study Will Explore Link Between Gum Disease and Heart Ills," *Medical Tribune News Service,* Jul. 22, 1997 (abstract only).

Offenbacher, et al., "Periodontal infection as a possible risk factor for preterm low birth weight," *J. Periodontol,* 67:1103–1113, Oct. 1996 (abstract only).

Papapanou, P.N., Periodontal diseases: epidemiology, *Ann. Periodontol.* 1(1):1–36, Nov. 1996 (abstract only).

Thorstensson, et al., "Medical status and complications in periodontal disease experience in insulin–dependent diabetics," *J. Clin. Periodontol,* 23:194–202, Mar. 1996 (abstract only).

Williams, et al., "The impact of new technologies to diagnose and treat periodontal disease," *J. Clin. Periodontol,* 23:299–305, Mar. 1996 (abstract only).

"Poor Dental Health and Chronic Bronchial Infection Linked to Stroke," *Reuters Information Services,* Westport, Sep. 9, 1997 (abstract only).

*Primary Examiner*—Gene Mancene
*Assistant Examiner*—Pedro Philogene
*Attorney, Agent, or Firm*—H. Dale Langley Jr.

[57] ABSTRACT

A method of treating systemic afflictions includes loading a dental floss with an active therapeutic agents and rubbing the floss against a mouth tissue to release the active therapeutic agent onto the tissue for penetration through the tissue. The active therapeutic agent is selected from the group consisting of zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. An additional therapeutic agent may also be loaded on the floss, for example, antimicrobials, antibiotics, antioxidants, anti-plaque agents, analgesics, anti-tarter agents, anti-caries agents, hemostatic agents, anti-inflammatory agents, hormones, bleaching agents and vitamins.

13 Claims, No Drawings

THERAPEUTIC DENTAL FLOSS FOR TREATING SYSTEMIC DISEASES

FIELD OF THE INVENTION

The present invention relates to the therapeutic use of dental floss and more particularly, to dental floss impregnated or coated with therapeutic agents, such as zinc salts, vitamins, antioxidants, fluoride salts, and other medicaments, for treating gingivitis and periodontal disease that may predispose individuals to other afflictions, for example, cardiovascular disease, stroke, premature births, HIV transmission, atherosclerosis, arthritis, and other chronic diseases.

BACKGROUND OF THE INVENTION

Before the onset of disease, healthy pink gingiva (gum tissue) surrounds the teeth, both holding them in place and preventing infectious material from entering the jaw bone or tooth itself. The tooth includes three regions known as the crown, neck, and root. Gingiva or gum tissue is the soft tissue covering the neck of the tooth. The area between the enamel and the gingiva is called the gingival crevice. The gums are under constant bacterial assault. Gingivitis develops when large masses of bacteria clog the gingival crevice.

Periodontal disease (gum disease) is one of the most prevalent chronic diseases affecting humans. Children as young as 5 years of age can have gum disease. By age 35, three out of four people are afflicted, and by age 65, an estimated 98 percent of Americans have periodontal disease." The word "periodontal" is derived from two Greek words that mean "around the tooth periodontal disease is caused by certain types of bacteria, forming a sticky, colorless, constantly forming film of bacteria called plaque. Plaque that is not removed can combine with other materials and harden into a rough, porous deposit called calculus (tartar). Calculus on the tooth surface (above the gum line) may not contribute to periodontal disease, but calculus on the neck or root surface (below the gums) makes removal of new plaque and bacteria more difficult. Bacteria in plaque produce metabolic by-products that diffuse into the immediate surrounding area, irritate the gingiva, and result in an inflammatory reaction. The gingiva then swells, becomes reddened, sensitive to touch and may bleed. It is not normal for gums to bleed when brushing or flossing. Bleeding gums is usually the first sign of gingivitis. Gingivitis is reversible. Gum disease occurs when the gingival crevice between the tooth and gum is more than three millimeters. As gingivitis progresses, the tissue surrounding the teeth is destroyed, the supporting collagen fibers begin to degenerate, and eventually the bone supporting the tooth socket degenerates and tooth loss can occur.

Periodontal disease can be prevented by practicing good oral hygiene. Daily tooth brushing and flossing are the most important weapons against the formation of plaque. Brushing teeth thoroughly at least twice a day helps remove plaque from the outer, inner, and chewing surfaces of the teeth. But careful brushing alone is not sufficient, because the bristles of the toothbrush cannot make contact with all parts or sides of the teeth. Dental floss helps to remove plaque from the crevices between the teeth that are often too deep to access with a brush.

Dental floss or tape is typically a multi-filament bundle of natural or synthetic fibers of varying thickness, usually in a continuous strand, sometimes coated with wax or other polymers and housed on a spool for ease of dispensing. Using dental floss to help remove plaque from the tooth surface is known in the art. It has been known in the art to coat or otherwise fix substances to dental floss for application of those substances to the teeth and gums to achieve therapeutic effects to the teeth and gums. Certain of these known are herein described:

Plaque Removal

The removal of plaque from teeth by the use of dentifrice formulations of toothpaste, gels, mouthwashes and dental floss is well described in the literature. For example, Lynch, U.S. Pat. Nos. 4,632,937 and 4,627,975 discloses coating the dental floss with a solution of monoalkyl and dialkyl ethers of dianhydrohexitols to reduce plaque accumulation. Wilkinson, U.S. Pat No. 4,819,675 discloses impregnating the dental floss with potassium hydrogen tartrate and potassium hydrogen citrate to remove plaque formation. Curtis, U.S. Pat. No. 5,033,488 discloses the use of anti-plaque agents such as chlorhexidine, hexachloraphene, cetylpyridinium chloride and benzothonium chloride, coated on polytetrafluoroethylene dental floss. The dental cleaning floss may also contain a coagulating agent, fluoride and anti-tartar agents such as tetrasodium pyrophosphate, sodium acid pyrophosphate or tetra potassium pyrophosphate. Greene, U.S. Pat. No. 5,065,861 discloses a dental floss dispenser in which baking soda and hydrogen peroxide attach to roughened dental floss as it is pulled out of the container.

Germicidal Agents

Dental floss has also been coated with germicidal agents to attack the microorganisms in the mouth. Corliss, U.S. Pat. No. 3,942,539 discloses dental floss pre-soaked with an antiseptic mouthwash solution. Rosenberger, U.S. Pat. Nos. 5,040,554, 5,280,796 and Re 35,439 discloses dental floss coated with sodium phenolate or 4-hexylresorcinol. In Britton, U.S. Pat. No. 5,226,434 it is disclosed that the anti-bacterial agent chlorhexidine is coated on the dental floss. Ahlert, U.S. Pat. No. 5,423,337 discloses the use of micro encapsulated calcium peroxide. Bowen, U.S. Pat. No. 5,603,921 discloses dental floss coated with chlorhexidine gluconate.

Antibiotics

Dental floss had also been coated with antibiotics. Hill, U.S. Pat. No. 5,098,711 discloses dental floss containing tetracycline, chlorhexidine, and polyvinyl pyrrolidone iodine complex as agents. Keller, U.S. Pat. Nos. 5,129,824 and 5,330,357 discloses tufted dental floss containing tetracycline.

Fluoride

The use of fluoride coated dental floss to inhibit the formation of dental caries is well known in the art. Guyton, U.S. Pat. No. 4,029,113 discloses the use of a fluorine compound coated on dental floss. Yost, U.S. Pat. No. 4,414, 990 discloses the use of a fluoride salt on dental floss. Newmann, U.S. Pat. Nos. 4,548,219 and 4,638,823 disclose the use of fluoride-coated dental floss. VanBeneden, U.S. Pat. No. 4,941,487 discloses a dental floss with patches of fluoride. Curtis, U.S. Pat. Nos. 5,033,488 and 5,209,251 discloses a dental cleaning floss containing a dentifrice, preferably a fluoride. Bottled water consumption has dramatically increased in the U.S., and is the usual source of drinking water in the world. The lack of fluoride in most bottled waters may lead to an increased risk of tooth decay. The use of fluoride salts in dental floss could overcome that deficiency.

Hemostatic Agents

Gingivitis frequently causes bleeding of the gums and hemostatic agents have been applied to dental floss. Vlock, U.S. Pat. No. 4,937,066 discloses the use of a dentifrice containing heavy metal salts to stop bleeding. Fisher, U.S. Pat. No. 5,635,162 discloses the use of a dentifrice containing heavy metal salts to maintain hemostasis. Curtis, U.S. Pat. Nos. 5,033,488 and 5,209,251 discloses the use of polytetrafluoroethylene as floss material and adds hemostatic agents.

Although dental floss has historically, at times, been coated with medications and other substances, the medications and substances have served primarily to treat afflictions of the teeth and gums. The soft tissue of the gums and mouth, however, provides superb penetrations to allow substances to enter the bloodstream. The present invention takes advantage of the penetration characteristics of the tissues of the mouth and gums to provide for application of a variety of therapeutic compositions that treat a variety of bodily afflictions, beyond mere therapy of the gums and mouth. The present invention also takes advantage of the ease of application of those therapeutic compositions via dental floss. The present invention, thus, provides a therapy for a variety of afflictions and is easy to use and apply. The invention is an improvement in the art and technology.

SUMMARY OF THE INVENTION

The present invention relates to dental floss impregnated or coated with therapeutic agents. In particular, this invention relates to the use of dental floss containing zinc salts to treat gingivitis and periodontal disease that may predispose individuals to cardiovascular disease, stroke, premature births, HIV transmission, atherosclerosis, and other systemic diseases. The present invention also contemplates the addition of antioxidants, vitamins, fluoride salts, and other medicaments to the zinc treated dental floss.

DETAILED DESCRIPTION OF THE INVENTION

The dental profession is well aware of the value of daily flossing of cleaning between the teeth to clean out food debris and remove dental plaque to prevent and remedy gum disease. For these purposes, the mechanical and abrasive action of the dental floss is of utmost importance. In fact, the focus of therapy with dental floss has conventionally been to provide such mechanical and abrasive action, and in some cases to apply certain medications intended to act on the gums and teeth directly controled by the floss.

Flossing alone, however, removes plaque, but does not treat gingivitis and periodontal disease, much less any other biologic functions of the body. It has been determined, in accordance with the present invention, that coating or impregnating the dental floss with a zinc salt and/or other therapeutic agents facilitates direct absorption of the medicaments by the periodontal tissues as the active material is wiped off the floss and onto the interdental spaces and gums. The dental floss of this invention allows the patient to self-administer the therapeutic agents directly to the periodontal tissues and treat the gingivitis and periodontal disease, as well as other systemic diseases.

The floss employed is natural or synthetic fibers of plastic, nylon, polyethylene, polypropylene and others, certain of which are known to the art. The thickness of the dental floss or tape, diameter of the filaments, and number of strands can be varied to either increase or decrease the concentration loading of therapeutic agents on the floss and that are, thus, available to be transferred from the dental floss to the oral tissues. The concentration of therapeutic agents loaded on the floss can be either increased or decreased, according to preparation steps taken, in order to reduce or increase the duration of effect of treatment or the amount of the application.

The active therapeutic materials with which the dental floss may be loaded include, for example, zinc salts, antioxidants, fluoride salts, and other medicaments. Suitable zinc salts may include, without limitation, zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. Suitable antioxidants may include, without limitation vitamin A, vitamin E, pyruvate B-carotene, selenium, N-acetylcysteine, vitamin C, superoxide dismutase (SOD), catalase, glutathione peroxidase, and glutathione reductase. Vitamin E encompasses a small group of related tocopherols. The suitable fluoride salts are, for example, sodium fluoride, stannous fluoride, sodium monofluorophosphate, amine fluoride, or any other suitable fluoride salt which is readily soluble in an aqueous environment.

Zinc Salts

Zinc is a trace element essential for biologic functions, such as growth, appetite, testicular maturation, skin integrity, mental activity, wound healing, and immune system maintenance. Zinc compounds have a long history of use as antiplaque and antitartar agents in toothpaste, gels and mouthwashes, as disclosed by Vinson in U.S. Pat. No. 4,022,880, Richey in U.S. Pat. No. 4,647,452 and Douglas in U.S. Pat. No. 5,104,644, but not as zinc coated dental floss for those purposes. Sipos, U.S. Pat. No. 4,160,821 discloses the use of zinc salts as a toothpaste to treat gingivitis. He noted that zinc chloride has been used as an astringent to achieve gingival retraction after swelling and that zinc acetate used as a mouth rinse can cause plaque to disappear. Fahim, U.S. Pat. No. 4,229,430 discloses a mouthwash composed of a zinc salt and ascorbic acid to treat gingivitis and periodontal disease. Shah, U.S. Pat. No. 4,325,939 discloses the use of sodium zinc citrate as a toothpaste, mouthwash or chewing gum to remove plaque and tartar from the teeth. Fisher, U.S. Pat. No. 5,625,162 discloses the use of zinc tartrate complexes in toothpaste and mouthwash to treat gingivitis and prevent gum bleeding. Williams, U.S. Pat. Nos. 5,456,902, 5,616,313, and 5,632,972 discloses the use of zinc salts in toothpastes and mouthwashes to treat gingivitis.

Zinc is an essential mineral found in every form of life on earth. Unlike other metals, zinc is virtually nontoxic. Zinc and its compounds have long been recognized as possessing certain therapeutic functions. Zinc compounds are acknowledged as astringents and beneficial in wound healing, reducing inflammation, and has antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding. Zinc acetate is used in eye drops to relieve chronic inflammation of the cornea in conjunctivitis. Zinc is believed to act as a protease inhibitor in its effect against rhinovirus infections that cause the common cold. Eby in U.S. Pat. Nos. 4,503,070, 4,956,385, Re 33,465, 5,095,035, and 5,409,905 uses zinc salts in lozenges as a cure for the common cold, due to the effect of zinc ions on viruses. Eby noted that zinc ions protect cell plasma membranes against damage induced by cytotoxic agents, and that zinc ions harden the cement substance of capillary epithelium so that pathological transcapillary movements of plasma protein is inhibited and local edema, inflammation and exudation are thereby reduced. Douglas, U.S. Pat. No. 5,104,644 discloses a mouthrinse containing the antimicrobial, zinc chloride, that has antiplaque, antitartar, and anti-inflammatory actions. He noted that zinc salts reduce gum swelling and reduce inflammation. Zinc salts attach to the cell wall of microorganisms and prevent them from adhering to each other and attaching to the tooth surface, thus preventing plaque from forming. Zinc has also been shown to inhibit acid production by microorganisms, thus impeding decalcification of the tooth. Zinc ions appear to inactivate the biochemical transport mechanisms of microorganisms by inhibiting the formation of ATP. Kelly, U.S. Pat. No. 5,624,675 discloses that zinc salts used in a genital lubricant can kill HIV-infected lymphocytes.

Zinc salts have been shown to be effective against the causes of gingivitis and periodontal disease. This is significant because it is now believed that periodontal disease can lead to other systemic diseases. Periodontal disease, usually a chronic Gram-negative infection, represent a previously unrecognized risk factor for atherosclerosis and thromboembolic events. Previous studies have demonstrated as association between periodontal disease severity and the risk of coronary heart disease and stroke. Researchers believe that periodontal disease, once established, provides a biological burden of endotoxin (lipopolysaccharide) and inflammatory cytokines (especially $TxA_2$, IL-1 beta, $PGE_2$, and TNF-alpha) which serve to initiate and exacerbate atherogenesis and thromboembolic events. Beck J, et al, *J. Periodontol* 1996;67:1123–1137. A study by the National Institutes of Health, led by Dr. Robert Genco, professor and chairman of Periodontology at the State University of New York suggest that infection and inflammation caused by gum disease may increase the risk of heart disease and that the inflammation caused by gum disease can contribute to the development of fatty plaque in heart arteries. The Health Professionals Follow-Up Study included a US national sample of 44,119 male health professionals (58% of whom were dentists) showed that those men who reported pre-existing periodontal disease had an increased risk of coronary heart disease. Joshipura K J, *J Dent Res* 1996 September;75(9):1631–6. Smoking, subgingival microorganisms and diabetes mellitus are risk factors for periodontal disease, which may confer risk for coronary heart disease and pre-term low birth weight. Papapanou P N, *Ann Periodontol* 1996 November;1 (1):1–36.

Untreated periodontal disease may account for a large proportion of premature births. Periodontal infection may account for as many as 18 percent of the 250,000 premature babies that are born weighing less than 5.5 pounds in the United States each year. If such births could be prevented by proper periodontal care and treatment of periodontal disease in women of childbearing age (18 to 34 years) the researchers stated that premature births might be reduced by abut 45,500 each year at a savings of almost $1 billion in intensive neonatal care. The bacteria found in periodontal disease appear to retard fetal growth by releasing into the woman's bloodstream toxins that reach the placenta and interfere with fetal development. In addition, the infection stimulates the woman's body to produce inflammatory chemicals, similar to those used to induce abortion, that can cause the cervix to dilate and set off uterine contractions. The risk of having a premature baby of low birth weight was at least 7.5 times as high for women with severe periodontal disease, and occurred in 5 percent of pregnancies and cost the country $5.7 billion a year. Offenbacher S, *J. Periodontol* 1996 October;67(10Suppl):1 103–13. While a birth weight of less than 3.3 pounds is a risk factor for cerebral palsy, findings suggest that maternal infections may account for 12 percent of cerebral palsy cases among children of normal birth weight. Grether J K, *JAMA* 1997;278:207–211.

Researchers at the University of Heidelberg found that patients with gingivitis and periodontal disease were two and a half times more likely to suffer a stroke or min-stroke than those with better oral health. Researchers have speculated that the large number of white blood cells produced by the body to fight infections may somehow cause atherosclerosis, or narrowed arteries. Treating the chronic periodontal disease may be an important way of preventing stroke. The presence of cavities had no influence on the incidence of stroke. Grau A J: Stroke 1997; 28:1724–1729.

A study involving insulin-dependent diabetics showed an association between renal disease, cardiovascular complications and periodontal disease. Thorstensson H, *J Clin Periodontol* 1996 March;23(3 Pt 1): 194–202. Periodontal disease has serious implications for other chronic diseases.

There are approximately 500,000 cases of AIDS reported to the Centers for Disease Control and Prevention (CDC) in Atlanta. A recent case documented HIV transmission from kissing. Researchers believe that blood from the man's bleeding gums was the source of the virus that entered the woman's bloodstream via her gum disease. CDC Morbidity and Mortality Weekly Report (1997;46:620–623). Zinc salts have both an astringent effect on gum tissue by decreasing swelling and bleeding and also an antiviral effect.

None of the foregoing patents mention or suggest the application of zinc salts to dental floss as a means of directly preventing and treating gingivitis and periodontal disease and subsequently preventing the development of other systemic diseases. In a preferred form of the invention, the dental floss is impregnated or coated with a zinc salt such as zinc acetate. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

Antioxidants

Antioxidants enhance the healing of infected and noninfected wounds by reducing the damage caused by oxygen radicals. Injured gum tissues undergo free radical reactions more quickly than do healthy ones. It has been suggested that free radicals play a role in collagen destruction in periodontal disease. Antioxidants are the main host defense produced in response to the production of free radicals. Antioxidant defense mechanisms include but are not limited to: vitamin E, pyruvate B-carotene, selenium, N-acetylcysteine, vitamin C, antioxyenzymes such as superoxide dismutase (SOD), catalase, glutathione peroxidase, and glutathione reductase together with the enzymes of the pentose monophosphate shunt pathway that regenerate NADPH. Pyruvate is one of the few antioxidants that readily enter cells, making it an ideal cytoplasmic antioxidant. Pyruvate alone or in combination with alpha tocopherol, vitamin E, inhibits reactive oxygen-induced damage. Vitamin E, a term that encompasses a small group of related tocopherols, is the major lipid-soluble antioxidant responsible for protecting the polyunsaturated fatty acids in membranes against lipid peroxidation. Tocopherols protect lipids by scavenging peroxyl radicals precluding further chain propagating steps. One or more antioxidants could be combined with the zinc salt to be impregnated or coated on the dental floss.

Other Active Agents

Other active components may be added to the dental floss to achieve the desired therapeutic effects. Individuals over 50 years of age need to supplement their diets with at least 25 micrograms of vitamin B-12 each day. If taken orally in a tablet with other vitamins or minerals the vitamin B-12 is destroyed by the stomach acids. One solution is to incorporate the vitamin B-12 into the dental floss.

Studies have shown that postmenopausal women taking estrogen replacement therapy (ERT) tend to retain their teeth. ERT has been shown to strengthen bones by slowing the rate of loss of bone mineral. The incorporation of estrogen into dental floss could strengthen the jawbone that supports the teeth.

In the 1980s the concept of locally delivering antibiotics to the periodontal pocket was introduced, and subsequent clinical trials have indicated that it is possible to reduce pocket depth and inflammation with tetracycline locally delivered to the periodontal pocket. Tetracycline is an inhibitor of collagenase, which destroys periodontal tissues. Clinical studies have also shown that it is possible to slow periodontal disease progression with non-steroidal anti-inflammatory medications such as flubiprofen, naproxen, ketoprofen and aspirin. Williams R C, *J Clin Periodontol* 1996 March;23(3 Pt 2):299–305. Systemically administered aspirin has been shown to reduce gingival inflammation and gingival crevice depth. Flemming T F, *J Clin Periodontol* 1996 March;23(3 Pt 1):153–9. Aspirin interferes with prostaglandin H2 synthase, the enzyme the body uses to manufacture prostaglandin. Prostaglandins are natural chemicals in the body that cause fever, headaches and inflammation. The addition of aspirin to dental floss could be used to treat periodontal disease.

A carrier or binder can alternatively be mixed with the zinc salt or other therapeutic agents to either speed or slow passage of the agents through the oral tissues and into the bloodstream. The binder for fixing the above material onto the floss may be, for example, a digestible, non-toxic, sterile, low melting material such as microcrystalline wax: preferably, the binder softens at mouth temperature. A method of loading the therapeutic dental floss with therapeutic agents and, if applicable, binder, is to melt the binder and dissolve the active materials therein, in a suitable receptacle. The floss is dispenses from a spool thereof and passed through the hot coating solution. The floss is coated with the solution in its passage therethrough. As the floss is removed from the solution, some amount of solution remains wetting the floss. The wetted floss is then allowed to cool. This cooling of the floss causes the solution to solidify, coating the floss both externally and in the interstices between threads. The amount of active material in the coating can be varied according to desired end use, as those skilled in the art will know and appreciate, such as, for example, by varying agent concentration of the solution, by speed of passage of the floss through melted solution, by speed of cooling, by makeup of the binder, and others. For use in treating gingivitis and periodontal disease, the concentration of the therapeutic agent(s) loaded on the floss may range from 25 to 75 percent by weight, the remainder being binder with the exact amount dependent on the binder's properties, and, in particular, the solubility of the active material therein. Of course, therapy for treatment of other ailments.

In various alternatives, the therapeutic agents may be encapsulated by means of microencapsulation techniques into small beads. Suitable encapsulation materials include, for example, polymeric coatings such as ethylcellulose and other coating polymers which coat and preserve the active ingredient until released by mechanical action of flossing between teeth and by enzymatic action of the saliva in the mouth. Polymeric coatings which are useful in the present invention include, without limitation, alkyl monoesters of poly(methyl vinyl ether maleic acid), polyvinyl pyrrolidones, acrylaminde/acrylate/butylaminoethyl mathacrylate polymers, terpolymers, copolymers, terpolyamines, and hydroxypropyl cellulose. Alternatively, the floss may be impregnated with therapeutic agents and subsequently coated with a water-soluble cellulose derivative, such as methyl cellulose or sodium carboxymethyl cellulose as a binder.

A surfactant may be loaded on the floss, as well. Suitable surfactants include, for example, sodium lauryl sulfate, sodium lauroyl sarcosinate, polyethylene glycol stearate, polyethylene glycol monostearate, coconut monoglyceride sulfonates, sodium alkyl sulfate, sodium alkyl sulfoacetates, copolymers of polyethylene and polybutylene, allypolyglycol, copolymers of polyoxybutylene and polysxylethylene. In other laternatives, the solution for immersing the floss and, consequently the floss loading, may include other additives such as dyes, flavorings, detergents, polishing agents.

The above-mentioned patents are hereby incorporated by reference.

Other variations of the present invention may suggest themselves to those skilled in the art, in light of the above-detailed description. For example, any zinc salt-containing compound may be employed. Further, the floss employed may be of any type, waxed or unwaxed.

Although illustrative embodiments of the invention have been shown and described, a wide range of modification, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A therapeutic floss for treatment of a systemic disease via absorption through a periodontal tissue coated in a saliva, the systemic disease being multi-system and not merely topical disease, comprising:

floss of substantially uniform thickness;

a therapeutic systemic agent that ionizes forming ions when placed in contact with the saliva; and a carrier that maintains the therapeutic systemic agent on the floss until the floss is placed in contact with the saliva and, upon contact with the saliva, encourages release of the ions of the therapeutic systemic agent maintained by the carrier, into solution with the saliva:

wherein the ions of the therapeutic systemic agent are absorbed from solution in the saliva through the periodontal tissue where the periodontal tissue contacts the saliva, and the ions treat the systemic disease.

2. The therapeutic floss of claim 1, wherein the floss is selected from the group consisting of single strand, multiple strands, and woven strands.

3. The therapeutic floss of claim 1, wherein the carrier is microcrystalline wax.

4. The therapeutic floss of claim 1, wherein the therapeutic systemic agent is selected from the group consisting of zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

5. The therapeutic floss of claim 1, wherein the therapeutic systemic agent is a zinc salt.

6. The therapeutic floss of claim 5, further comprising:

an additional therapeutic agent maintained by the carrier, wherein the additional therapeutic agent is selected from the group consisting of antimicrobials, antibiotics, antioxidants, anti-plaque agents, analgesics, anti-tartar agents, anti-caries agents, hemostatic agents, anti-flammatory agents, hormones, bleaching agents and vitamins.

7. A method of treating a systemic afflication, the systemic affliction being multi-system and not merely topical affliction, comprising the steps of:

loading a floss with an active therapeutic agent in concentrations sufficient for treating the systemic affliction;

contacting the floss and active therapeutic agent loaded thereon with a saliva in contact with a periodontal tissue;

rubbing the floss against the periodontal tissue to encourage contact of the active therapeutic agent with the saliva; and releasing ions of the active therapeutic agent into solution with the saliva for absorption by and penetration through the periodontal tissue, in order that the ions can treat the systemic affliction.

8. The method of claim 7, wherein the active therapeutic agent is a zinc salt.

9. The method of claim 8, wherein the active therapeutic agent is selected from the group consisting of zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

10. The method of claim 7, further comprising the step of coating the floss with a binder.

11. The method of claim 7, wherein the active therapeutic agent is disbursed in the binder and the binder is released from the floss when the floss is moved against the mouth tissue so that the binder deposits on the mouth tissue and the active therapeutic agent is released from the binder onto the mouth tissue.

12. The method of claim 11, wherein the floss is loaded with an additional therapeutic agent.

13. The method of claim 7, further comprising the step of loading the floss with an additional therapeutic agent selected from the group consisting of antimicrobials, antibiotics, antioxidants, anti-plaque agents, analgesics, anti-tarter agents, anti-caries agents, hemostatic agents, anti-inflammatory agents, hormones, bleaching agents and vitamins.

* * * * *